United States Patent [19]

Berg

[11] Patent Number: 5,447,608
[45] Date of Patent: Sep. 5, 1995

[54] SEPARATION OF 2-PENTANOL, 3-METHYL-2-BUTANOL AND 1-BUTANOL BY AZEOTROPIC DISTILLATION

[75] Inventor: Lloyd Berg, 1314 South Third Ave., Bozeman, Mont. 59715

[73] Assignee: Lloyd Berg, Bozeman, Mont.

[21] Appl. No.: 283,640

[22] Filed: Aug. 1, 1994

[51] Int. Cl.$^6$ .................. B01D 3/36; C07C 29/82
[52] U.S. Cl. ............................. 203/57; 203/60; 203/62; 203/63; 203/64; 203/68; 203/69; 203/70; 568/913
[58] Field of Search ................. 203/62, 60, 63, 57, 203/68, 69, 70, 64; 568/913

[56] References Cited

U.S. PATENT DOCUMENTS

| | | | |
|---|---|---|---|
| 2,483,246 | 9/1949 | Stribley | 203/60 |
| 2,500,329 | 3/1950 | Steitz | 203/69 |
| 5,338,410 | 8/1994 | Berg | 203/60 |

*Primary Examiner*—Wilbur Bascomb, Jr

[57] ABSTRACT

3-Methyl-2-butanol, 2-pentanol and 1-butanol are difficult to separate by conventional distillation or rectification because of the proximity of their boiling points. Mixtures of these three can be readily separated from each other by azeotropic distillation. Effective agents are hexyl acetate, hexane and 3-methyl pentane.

2 Claims, No Drawings

SEPARATION OF 2-PENTANOL, 3-METHYL-2-BUTANOL AND 1-BUTANOL BY AZEOTROPIC DISTILLATION

FIELD OF THE INVENTION

This invention relates to a method for separating 2-pentanol, 3-methyl-2-butanol and 1-butanol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the-azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of alcohols, e.g. the Fischer-Tropsch process which produces a series of homologous alcohols. Three of the commonest alcohols usually present are 3-methyl-2-butanol, B.P.=112° C., 2-pentanol, B.P.=120° C. and 1-butanol, B.P.=118° C. The relative volatility of 3-methyl-2-butanol and 2-pentanol is 1.4, between 1-butanol and 2-pentanol it is 1.08 and between 3-methyl-2-butanol and 1-butanol it is 1.25.

When these three occur together as a mixture, they are impossible to separate by conventional rectification. Azeotropic distillation would be an attractive method of effecting this separation if agents can be found that (1) will create a large apparent relative volatility between them and (2) are easy to recover from 2-pentanol. Table 2 shows the relative volatility required to obtain products of 99% purity. With no agent, the relative volatilities are 1.08, 1.4 and 1.25, see Table 3. Table 2 shows that with a relative volatility of 1.08, 160 actual plates would be required. With an agent giving a relative volatility of 1.4, only 36 actual plates are required; with a relative volatility of 1.95, only 19 actual plates are needed.

TABLE 2

Theoretical and Actual Plates Required vs. Relative Volatility for 3-Methyl-2-butanol - 2-Pentanol - 1-Butanol Separation

| Relative Volatility | Theoretical Plates Required At Total Reflux, 99% Purity | Actual Plates Required 75% Efficiency |
|---|---|---|
| 1.08 | 120 | 160 |
| 1.4 | 27 | 36 |
| 1.6 | 20 | 27 |
| 1.95 | 14 | 19 |

OBJECTIVE OF THE INVENTION

The object of this invention is to provide a process or method azeotropic distillation that will enhance the relative volatility between 3-methyl-2-butanol, 2-pentanol and 1-butanol in their separation as a mixture in a rectification column. It is a further object of this invention to identify organic compounds which in addition to the above constraints, are stable, can be separated from the alcohols and recycled to the azeotrope column with little decomposition.

SUMMARY OF THE INVENTION

The objects of this invention are to provide a process for separating a mixture of 3-methyl-2-butanol, 2-pentanol and 1-butanol which entails the use of certain organic compounds as the agent in azeotropic distillation.

DETAILED DESCRIPTION OF THE INVENTION

I have discovered that certain organic compounds will greatly improve the relative volatility between 3-methyl-2-butanol, 2-pentanol and 1-butanol and permit the separation of these alcohols by rectification when employed as the agent in azeotropic distillation. Table 3 lists the compounds that I have found to be effective. The agents that remove 2-pentanol as bottoms product are 2-pentanone, n-propyl acetate, heptane, acetal, 2,2-dimethoxy propane, butyl formate, ethyl acetate, benzonitrile, t-amyl methyl ether, isobutyl acetate, methyl amyl acetate, amyl acetate, hexyl acetate, dipentene, d-limonene, terpinolene, 2,3,4-trimethyl pentane, dicyclopentadiene, octane, cumene, hexane, p-xylene, m-xylene, o-xylene,

TABLE 3

Effective Azeotropic Distillation Agents For Separating 2-Pentanol From 3-Methyl-2-butanol And 1-Butanol

| | Relative Volatility | | |
|---|---|---|---|
| Compounds | 1-BuOH 2-PnOH | 3-Me-2-BuOH 2-PnOH | 3-Me-2-BuOH 1-BuOH |
| None | 1.08 | 1.4 | 1.25 |
| 3-Pentanone | 1.17 | 1.9 | 1.6 |
| n-Propyl acetate | 1.25 | 1.36 | 1.07 |
| Acetal | 1.17 | 1.53 | 1.32 |
| 2,2-Dimethoxy propane | 1.25 | 1.6 | 1.32 |
| Butyl formate | 1.25 | 1.35 | 1.08 |
| Ethyl acetate | 1.17 | 1.4 | 1.17 |
| Benzonitrile | 1.17 | 1.32 | 1.15 |
| t-Amyl methyl ether | 1.17 | 1.34 | 1.14 |
| Isobutyl acetate | 1.17 | 1.36 | 1.14 |
| Methyl amyl acetate | 2.1 | 2.3 | 1.1 |

TABLE 3-continued

Effective Azeotropic Distillation Agents For Separating 2-Pentanol From 3-Methyl-2-butanol And 1-Butanol

| Compounds | Relative Volatility | | |
|---|---|---|---|
| | 1-BuOH 2-PnOH | 3-Me-2-BuOH 2-PnOH | 3-Me-2-BuOH 1-BuOH |
| Amyl acetate | 1.75 | 1.65 | 1.0 |
| ** Ethylene glycol ethyl ether acetate | 1.17 | 0.8 | 0.7 |
| Hexyl acetate | 1.65 | 1.8 | 1.04 |
| Dipentene | 1.3 | 1.65 | 1.23 |
| d-Limonene | 1.3 | 1.35 | 1.0 |
| Terpinolene | 1.4 | 1.4 | 1.0 |
| ** Carane | 1.65 | 1.0 | 0.6 |
| 2,3,4-Trimethyl pentane | 1.3 | 1.3 | 1.0 |
| Dicyclopentadiene | 1.3 | 1.18 | 0.9 |
| Octane | 1.3 | 1.35 | 1.0 |
| Cumene | 1.3 | 1.4 | 1.05 |
| Hexane | 1.43 | 1.63 | 1.13 * |
| p-Xylene | 1.3 | 1.43 | 1.05 |
| m-Xylene | 1.3 | 1.32 | 1.0 |
| o-Xylene | 1.3 | 1.43 | 1.08 |
| Toluene | 1.3 | 1.38 | 1.06 |
| Ethyl benzene | 1.4 | 1.35 | 0.9 |
| Cyclopentane | 1.3 | 1.55 | 1.2 |
| Cyclohexane | 1.35 | 1.42 | 1.1 |
| 1-Hexene | 1.3 | 1.6 | 1.25 |
| Heptane | 1.3 | 1.3 | 1.0 |
| Methyl cyclohexane | 1.3 | 1.53 | 1.15 |
| ** 3-Methyl pentane | 1.95 | 1.72 | 1.0 * |
| 2-Nitropropane | 1.3 | 1.4 | 1.15 |
| ** Methyl ethyl ketoxime | 1.6 | 1.0 | 0.6 |
| 1-Octene | 1.4 | 1.4 | 1.0 |

\* Data From Multiplate Rectification Column
\*\* Brings 1-butanol out as overhead product toluene, ethyl benzene, cyclopentane, cyclohexane, 1-hexene, methyl cyclohexane, 2-nitropropane and 1-octene. The agents that remove 1-butanol as overhead product are ethylene glycol ethyl ether acetate, methyl ethyl ketoxime, carane and 3-methyl pentane

THE USEFULNESS OF THE INVENTION

The usefulness or utility of this invention can be demonstrated by referring to the data presented in Tables 2 and 3. All of the successful agents show that 3-methyl-2-butanol, 2-pentanol and 1-butanol can be separated one from another by means of azeotropic distillation in a rectification column and that the ease of separation as measured by relative volatility is considerable.

WORKING EXAMPLES

EXAMPLE 1

Forty grams of a mixture comprising 10% 3-methyl-2-butanol, 40% 2-pentanol and 50% 1-butanol and 40 grams of hexyl acetate were placed in a vapor liquid equilibrium still and refluxed for six hours. The vapor composition was 10.3% 3-methyl-2-butanol, 36.1% 2-pentanol and 53.6% 1-butanol; the liquid composition was 7.9% 3-methyl-2-butanol, 49.6% 2-pentanol and 42.5% 1-butanol. This is a relative volatility of 1-butanol to 2-pentanol of 1.65, 3-methyl-2-butanol to 2-pentanol of 1.8 and 3-methyl-2-butanol to 1-butanol of 1.04.

EXAMPLE 2

One hundred grams of a mixture comprising 10% 3-methyl-2-butanol, 40% 2-pentanol and 50% 1-butanol and 140 grams of hexane were placed in the stillpot of a 5.6 theoretical plate glass perforated plate rectification column and refluxed for 1.5 hours. The overhead composition was 10.5% 3-methyl-2-butanol, 8.2% 2-pentanol and 81.3% 1-butanol; the bottoms composition was 3.5% 3-methyl-2-butanol, 42.3% 2-pentanol and 54.2% 1-butanol. This is a relative volatility of 3-methyl-2-butanol to 2-pentanol of 1.63; of 3-methyl-2-butanol to 1-butanol of 1.13 and 1-butanol to 2-pentanol of 1.43.

EXAMPLE 3

Forty grams of a mixture comprising 10% 3-methyl-2-butanol, 40% 2-pentanol and 50% 1-butanol and 100 grams of 3-methyl pentane were placed in the stillpot of a 5.6 theoretical plate glass perforated plate rectification column and refluxed for three hours. The overhead composition was 7.7% 3-methyl-2-butanol, 1.6% 2-pentanol and 90.7% 1-butanol; the bottoms composition was 8.7% 3-methyl-2-butanol, 39.3% 2-pentanol and 52.0% 1-butanol. This is a relative volatility of 3-methyl-2-butanol to 2-pentanol of 1.72; of 3-methyl-2-butanol to 1-butanol of 1.0 and 1-butanol to 2-pentanol of 1.95.

I claim:

1. A method for recovering 2-pentanol from a mixture of 2-pentanol, 3-methyl-2-butanol and 1-butanol which comprises distilling a mixture of 2-pentanol, 3-methyl-2-butanol and 1-butanol in the presence of an azeotrope forming agent, recovering the 3-methyl-2-butanol, 1-butanol and the azeotrope forming agent as overhead product and obtaining the 2-pentanol as bottoms product, wherein said azeotrope forming agent consists of one material selected from the group consisting of acetal, n-propyl acetate, 2,2-dimethoxy propane, ethyl acetate, benzonitrile, t-amyl methyl ether, isobutyl acetate, methyl amyl acetate, amyl acetate, 2-nitropropane, hexyl acetate, dipentene, d-limonene, terpinolene, dicyclopentadiene, and cumene.

2. A method for separating 1-butanol from a mixture of 1-butanol, 3-methyl -2-butanol and 2- pentanol which comprises distilling a mixture of 1-butanol, 3-methyl-2-butanol and 2-pentanol in the presence of an azeotrope forming agent, recovering the 1-butanol and the azeotrope forming agent as overhead product and obtaining the 3-methyl-2-butanol and the 2-pentanol as bottoms product, wherein said azeotrope forming agent consists of one material selected from the group consisting of ethylene glycol ethyl ether acetate, methyl ethyl ketoxime, carane and 3-methyl pentane.

* * * * *